United States Patent [19]

Yoshihara et al.

[11] Patent Number: 5,750,099

[45] Date of Patent: May 12, 1998

[54] TWO-PACK TYPE KERATINOUS FIBER TREATING COMPOSITION

[75] Inventors: Toru Yoshihara; Emi Chugun, both of Tokyo, Japan

[73] Assignee: Kao Corporation, Tokyo, Japan

[21] Appl. No.: 462,550

[22] Filed: Jun. 5, 1995

Related U.S. Application Data

[63] Continuation of Ser. No. 170,663, Dec. 16, 1993, abandoned, which is a continuation of Ser. No. 928,030, Aug. 11, 1992, abandoned.

[30] Foreign Application Priority Data

Aug. 13, 1991 [JP] Japan ............... 3-203018

[51] Int. Cl.$^6$ ............... A61K 7/06; A61K 7/13
[52] U.S. Cl. ............... 424/70.17; 424/70.19; 424/70.21; 424/70.22; 132/208; 8/405
[58] Field of Search ............... 424/70.1, 70.11, 424/70.2, 70.15, 70.17; 8/405; 132/208

[56] References Cited

U.S. PATENT DOCUMENTS

| | | | |
|---|---|---|---|
| 4,058,131 | 11/1977 | Crawford | 424/70 |
| 4,075,131 | 2/1978 | Sterling | 424/70 |
| 4,080,310 | 3/1978 | Ng et al. | 424/70 |
| 4,366,827 | 1/1983 | Madrange | 132/7 |
| 4,425,132 | 1/1984 | Grollier | 424/70 |
| 4,602,648 | 7/1986 | Syed | 424/70 |
| 4,820,511 | 4/1989 | Hoeffkes | 424/71 |
| 4,855,130 | 8/1989 | Konrad | 424/71 |
| 5,032,402 | 7/1991 | Digenis | 424/448 |

FOREIGN PATENT DOCUMENTS

| | | | |
|---|---|---|---|
| 0269107 | 6/1988 | European Pat. Off. | |
| 0437114 | 7/1991 | European Pat. Off. | |
| 9103513 | 7/1992 | Germany | |
| 64-75411 | 8/1964 | Japan | |
| 0040614 | 12/1979 | Japan | 424/70 |
| 0210006 | 12/1983 | Japan | 424/70 |
| 1063611 | 4/1986 | Japan | 424/70 |
| 2114616 | 8/1983 | United Kingdom | |

*Primary Examiner*—Sally Gardner-Lane
*Attorney, Agent, or Firm*—Sughrue, Mion, Zinn, Macpeak & Seas, PLLC

[57] ABSTRACT

A two-pack type keratinous fiber treating composition where the first pack contains an organic solvent and an acid and the second pack contains a cationic polymer and/or an amphoteric polymer. When keratinous fibers are treated with the keratinous fiber treating composition, the cationic polymer and the amphoteric polymer contained in the second pack penetrate into the keratinous fibers which have been swollen by the first pack. Thus, conditioning effects (for example, softness, moistness, smoothness and ease of arrangement of the hair) are exerted on the keratinous fibers for a prolonged period of time.

4 Claims, No Drawings

TWO-PACK TYPE KERATINOUS FIBER TREATING COMPOSITION

This is a Continuation of application Ser. No. 08/170,663 filed on Dec. 16, 1993 (abandoned), which is a continuation of application Ser. No. 07/928,030 filed Aug. 11, 1992 (abandoned).

FIELD OF THE INVENTION

This invention relates to a two-pack type keratinous fiber treating composition capable of exerting long-lasting conditioning effects of imparting a good texture including softness, moistness and smoothness to keratinous fibers (such as the hair) and of making the arrangement of keratinous fibers, which are liable to spread out widely, easy, as well as a method for treating keratinous fibers using the same.

BACKGROUND OF THE INVENTION

Conditioning agents such as rinses and various treatments are commonly used at home in order to impart good texture, including softness, moistness and smoothness, to shampooed hair. Treatment of the hair with these conditioning agents makes conditioning components (for example, cationic polymers, cationic surfactants, fats and oils, silicone derivatives, humectants, proteins and hydrolysates thereof, animal or vegetable extracts, etc.) remain on the surface or the external layer of the hair. In beauty parlors, on the other hand, conditioning agents having the same function as the conditioning agents for home use are applied with heating, for example, with a steamer, to increase the amount of conditioning components remaining on the hair, to attempt to give an excellent feel upon use which is superior to that obtained at home. However, these conditioning effects are lost after shampooing once or twice. In recent years, people have tended shampoo their hair almost everyday, though frequency varies depending on the generation. Accordingly, physical damage caused by rubbing and tangling of the hair during shampoo due to the disappearance of conditioning effects has become a serious problem.

JP-A-64-75411 discloses a heating-type hair treatment agent where a composition comprising a cationic polymer and a cysteine derivative is combined with a heating treatment (the term "JP-A" as used herein means an "unexamined published Japanese patent application"). According to this patent, the disclosed hair treatment agent can improve the texture of the hair within a relatively short period of time and, achieve good wave of the hair, thus relieving damage to the hair. However, the heating-type hair treatment agent described therein only has poor moisture retention ability upon drying and thus does not impart sufficient softness or satisfactory moistness.

On the other hand, JP-A-56-100710 corresponding to U.S. Pat. No. 4,366,827 and JP-A-58-150506 corresponding to GB-B-2,114,616 describe that conditioning effects (for example, imparting softness) can be exerted on the hair by a permanent waving method, where a first composition containing a reducing agent and a cationic polymer is applied to the hair and subsequently a second composition containing an oxidizing agent and an anionic surfactant is applied, as well as compositions usable therein. However, the method and compositions described in these patents are also disadvantageous in that the conditioning effects cannot be sustained for a sufficiently long period of time.

SUMMARY OF THE INVENTION

It is an object of the present invention to provide a novel keratinous fiber treating composition capable of exerting long-lasting conditioning effects of imparting good texture including softness, moistness and smoothness to keratinous fibers (such as the hair) and of making the arrangement of keratinous fibers, which are liable to spread out widely, easy, as well as a method for treating keratinous fibers using the same.

Under these circumstances, the present inventors conducted extensive studies in order to solve the above-mentioned problems. As a result, they found that when keratinous fibers are treated with a keratinous fiber treating composition consisting of a first pack containing an organic solvent and an acid and a second pack containing a cationic polymer and/or an amphoteric polymer, a large amount of the cationic polymer and/or amphoteric polymer penetrates into the keratinous fibers, which have been highly swollen with the first pack, and adheres thereto, thus exerting long-lasting conditioning effects on the keratinous fibers. The present invention has been completed based on this finding.

Accordingly, the present invention provides a two-pack type keratinous fiber treating composition consisting of a first pack containing an organic solvent and an acid and a second pack containing a cationic polymer and/or an amphoteric polymer.

DETAILED DESCRIPTION OF THE INVENTION

The organic solvent contained in the first pack of the composition of the present invention is employed in order to dissolve the acid, which will be described hereinafter, so as to promote the penetration of the acid into keratinous fibers. As such an organic solvent, those represented by the following general formulae (I) and (II) are exemplified:

$$R^1-(OCH_2CH_2)_p-(OCH_2\underset{|}{CH})_q-Z \qquad (I)$$
$$(CH_2)_r-Y$$

wherein

R$^1$ represents a hydrogen atom, a straight-chain or branched alkyl group having from 1 to 4 carbon atoms, a group

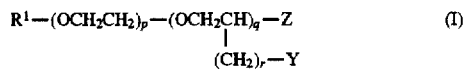

or a group

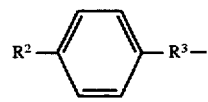

wherein

R$^2$ represents a hydrogen atom, a methyl group or a methoxy group; and

R$^3$ represents —CH$_2$—, —C(CH$_3$)$_2$—, —CH$_2$CH$_2$—, —CH$_2$CH(CH$_3$)—, —CH$_2$CH$_2$CH$_2$— or —CH=CHCH$_2$—;

p, q and r represent each an integer of from 0 to 5; and

Y and Z each represent a hydrogen atom or a hydroxyl group, provided that the equation p=q=r=0 is not satisfied when both of R$^1$ and Z are hydrogen atoms, i.e., when R$^1$ and Z are both hydrogen atoms, at least one of p, q, and r must be present;

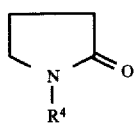
(II)

wherein $R^4$ represents a straight-chain or branched alkyl group having from 1 to 18 carbon atoms.

Examples of such an organic solvent include ethanol, isopropanol, n-propanol, n-butanol, isobutanol, ethylene glycol, propylene glycol, 1,3-butanediol, benzyl alcohol, cinnamyl alcohol, phenethyl alcohol, p-anisyl alcohol, p-methylbenzyl alcohol, phenoxyethanol, 2-benzyloxyethanol, methyl carbitol, ethyl carbitol, propyl carbitol, butyl carbitol, triethylene glycol monoethyl ether, triethylene glycol monobutyl ether, glycerol, N-methylpyrrolidone, N-octylpyrrolidone and N-laurylpyrrolidone.

In the present invention, it is preferable that the content of the organic solvent in the first pack of the present invention ranges from 5 to 50% (by weight, the same will apply hereinafter), still preferably from 2 to 30%, based on the total weight of the first pack. When the content of the organic solvent is less than 0.5%, sufficient effects can be hardly achieved. When its content exceeds 50%, on the other hand, the effects are scarcely improved over the use of a lesser amount within the preferred range. The above organic solvent may be used either alone or as a combination of two of more thereof.

It is preferable to use a weak acid as the acid contained in the first pack of the composition according to the present invention, since the hair per se has an ion exchange ability. Examples of such a weak acid include citric acid, glycolic acid, succinic acid, tartaric acid, lactic acid, acetic acid, fumaric acid, malic acid, levulinic acid, butyric acid, valeric acid, oxalic acid, maleic acid, phthalic acid, mandelic acid and phosphoric acid.

The content of the acid(s) in the first pack of the composition according to the present invention preferably ranges from 0.01 to 25.0%, still preferably from 0.1 to 15.0%, based on the total weight of the first pack. When a weak acid is used, it is preferable to add such acid together with, for example, its sodium, potassium or ammonium salt, since a buffer action can thus be imparted to the system.

The pH value of the first pack of the present invention, which contains the above-mentioned organic solvent and acid, preferably ranges from 2.0 to 5.0, still more preferably from 2.5 to 4.0. The above acid may be used either alone or as a combination of two or more thereof.

As examples of the cationic polymer contained in the second pack of the present invention, cationized cellulose derivatives, cationic starches, cationized guar gum derivatives, diallyl quaternary ammonium salt/acrylamide copolymers, diallyl quaternary ammonium salt polymers, quaternized polyvinyl pyrrolidone derivatives, and cationic silicone polymers can be exemplified.

As the cationized cellulose derivatives, among these substances, those represented by the following general formula (III) are preferable.

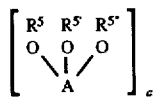
(III)

wherein

A represents a glucose unit;

a is an integer of from 50 to 20,000; and

Each $R^5$, each $R^{5'}$, and each $R^{5''}$, which may be the same or different, each represents a substituent group represented by the following general formula (IV).

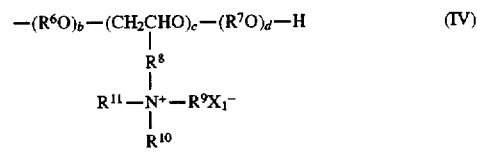
(IV)

wherein $R^6$ and $R^7$ each represent an alkylene group having 2 or 3 carbon atoms;

b is an integer of from 0 to 10;

c is an integer of from 0 to 3;

d is an integer of from 0 to 10;

$R^8$ represents an alkylene or hydroxyalkylene group having from 1 to 3 carbon atoms;

$R^9$, $R^{10}$ and $R^{11}$ each may be the same or different and each represents an alkyl, aryl or aralkyl group each having up to 20 carbon atoms or forms a heterocycle containing a nitrogen atom in the formula; and $X_1$ represents an anion (for example, chlorine, bromine, iodine, sulfate, sulfonate, methylsulfate, phosphate or nitrate).

The degree of cation substitution of the cationized cellulose derivative ranges from 0.01 to 1. Namely, the average value of c per glucose unit ranges from 0.01 to 1, preferably from 0.02 to 0.5. The total of b+d ranges from 1 to 3 on the average. A degree of substitution smaller than 0.01 is insufficient. Although the degree of substitution may exceed 1, it is preferably smaller than 1 from the viewpoint of reaction yield. For example, it is preferable that $R^9$, $R^{10}$ and $R^{11}$ all represent methyl groups or two of them are short chain alkyl groups having 1 to 3 carbon atoms and the remaining one is a long chain alkyl group having 10 to 20 carbon atoms. The molecular weight of the cationized cellulose derivative used herein preferably ranges from 100,000 to 8,000,000 (weight average).

As the cationic starches, those represented by the following general formula (V) are preferably used.

$$B + O - R^{12} - \overset{R^{13}}{\underset{R^{15}}{N^+}} - R^{14}.X_2^-]_e \quad (V)$$

wherein

B represents a starch chain;

$R^{12}$ represents an alkylene or hydroxyalkylene group, preferably, a $C_{1-3}$ alkylene or $C_{1-3}$ hydroxyalkylene group;

$R^{13}$, $R^{14}$ and $R^{15}$ may be the same or different and each represents an alkyl, aryl or aralkyl group each having up to 10 carbon atoms or forms a heterocycle containing a nitrogen atom in the formula;

$X_2$ represents an anion (for example, chlorine, bromine, iodine, sulfate, sulfonate, methylsulfate, phosphate or nitrate); and e is a positive integer, preferably, an integer of from 1 to 5.

The degree of cation substitution of the cationic starch can range from 0.01 to 1. Namely, it is preferable that from 0.01 to 1, still more preferably from 0.02 to 0.5, cation groups are introduced per glucose unit. A degree of substitution less than 0.01 is insufficient. Although the degree of substitution may exceed 1, it is preferably smaller than 1 from the viewpoint of reaction yield.

As the cationized guar gum derivatives, those represented by the following general formula (VI) are preferable.

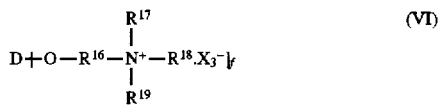

wherein

D represents a guar gum chain;

$R^{16}$ represents an alkylene or hydroxyalkylene group, preferably, a $C_{1-3}$ alkylene or $C_{1-3}$ hydroxyalkylene group;

$R^{17}$, $R^{18}$ and $R^{19}$ may be the same or different and each represents an alkyl, aryl or aralkyl group each having up to 10 carbon atoms or forms a heterocycle containing a nitrogen atom in the formula;

$X_3$ represents an anion (for example, chlorine, bromine, iodine, sulfate, sulfonate, methylsulfate, phosphate or nitrate); and f is a positive integer, preferably, an integer of from 1 to 5.

With respect to the degree of cation substitution of the cationized guar gum derivative, it is preferable that from 0.01 to 1, still more preferably from 0.02 to 0.5, cation groups are introduced per sugar unit. Cationic polymers of this type are described in JP-B-58-35640 corresponding to U.S. Pat. No. 4,298,494, JP-B-60-46158 corresponding to U.S. Pat. No. 5,037,818 and JP-A-58-53996 corresponding to U.S. Pat. No. 4,364,837 and are commercially available from, for example, Meyhall Chemical AG under the trademark "JAGUAR" (the term "JP-B" as used herein means an "examined Japanese patent publication").

As the diallyl quaternary ammonium salt polymers or diallyl quaternary ammonium salt/acrylamide copolymers, those represented by the following general formulae (VII) and (VIII) are preferable.

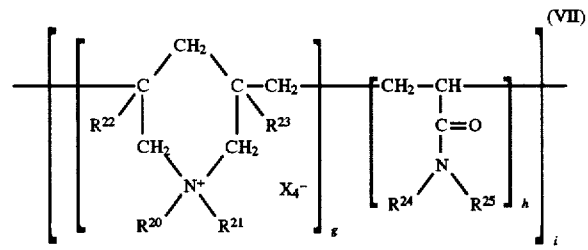

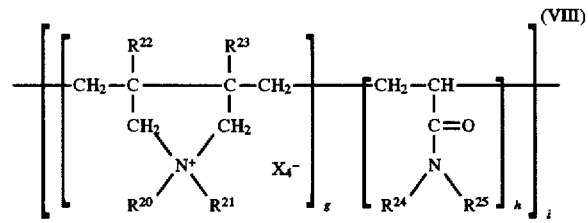

wherein $R^{20}$ and $R^{21}$ may be the same or different and each represents a hydrogen atom or an alkyl, aryl, hydroxyalkyl, amidoalkyl, cyanoalkyl, alkoxyalkyl or carboalkoxy alkyl group, each having up to 18 carbon atoms;

$R^{22}$, $R^{23}$, $R^{24}$ and $R^{25}$ may be the same or different and each represents a hydrogen atom, a lower alkyl ($C_1$ to $C_3$) group, or a phenyl group;

$X_4$ represents an anion (for example, chlorine, bromine, iodine, sulfate, sulfonate, methylsulfate or nitrate);

g is an integer of from 1 to 50;

h is an integer of from 0 to 50; and i is an integer of from 150 to 8,000.

The molecular weight of the diallyl quaternary ammonium salt/acrylamide copolymer may range from about 30,000 to 2,000,000, preferably from 100,000 to 1,000,000 (weight average).

As the quaternized polyvinyl pyrrolidone derivatives, those represented by the following general formula (IX) are preferable.

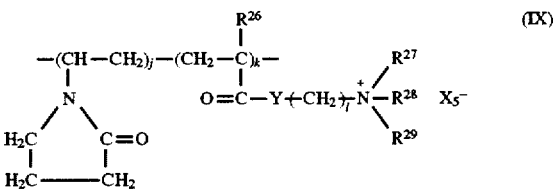

wherein $R^{26}$ represents a hydrogen atom or an alkyl group having from 1 to 3 carbon atoms;

$R^{27}$, $R^{28}$ and $R^{29}$ may be the same or different and each represents a hydrogen atom or an alkyl ($C_1$ to $C_4$), hydroxyalkyl, amidoalkyl, cyanoalkyl, alkoxyalkyl or carboalkoxyalkyl group, preferably, a hydrogen atom, a $C_{1-4}$ alkyl group, or a hydroxyalkyl, amidoalkyl, cyanoalkyl, alkoxyalkyl or carboalkoxyalkyl group each having 1 to 18 carbon atoms;

Y represents an oxygen atom or an NH group;

$X_5$ represents an anion (for example, chlorine, bromine, iodine, sulfate, sulfonate, $C_1$ to $C_4$ alkylsulfate, phosphate or nitrate);

l is an integer of from 1 to 10; and j+K is an integer of from 20 to 8,000.

The molecular weight of the quaternized polyvinyl pyrrolidone derivative may range from about 10,000 to 2,000,000, preferably from 50,000 to 1,500,000 (weight average).

The content of cationic nitrogen originating from a cationic polymer contained in the above-mentioned vinyl polymer may range from 0.004 to 0.2%, preferably from 0.01 to 0.15%, based on the vinyl polymer. When this content is lower than 0.004%, sufficient effects can hardly be achieved. On the other hand, a cationic nitrogen content exceeding 0.2% might cause coloration of the vinyl polymer and, further, is disadvantageous from an economical viewpoint, though a good function is observed in this case.

A typical example of the cationic silicone polymers is one represented by the following general formula (X). This polymer has an average molecular weight of from 3,000 to 100,000 (weight average) and is described in the CTFA dictionary (the Cosmetic Ingredient Dictionary, U.S.A., Third Ed.) under the name Amodimethicone.

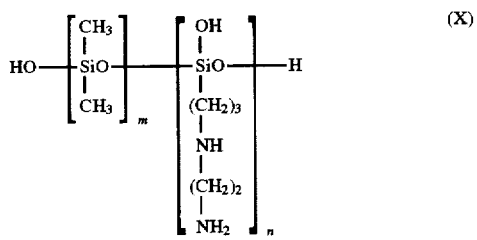

wherein m and n each represent an integer which is defined depending on the molecular weight.

The above cationic silicone polymer is preferably used in the form of an aqueous emulsion. Such an aqueous emulsion may be prepared in accordance with, for example, a method as described in JP-B-56-38609 corresponding to U.S. Pat. No. 4,228,054 which comprises emulsion-polymerizing a cyclic diorganopolysiloxane with an organodialkoxysilane having an amino alkyl group and a hydroxy, hydroxyalkyl, oxyalkylene or polyoxyalkylene group in the presence of a quaternary ammonium salt surfactant and water.

The amphoteric polymer contained in the second pack of the composition according to the present invention may be prepared by copolymerizing an acidic vinyl monomer with a basic vinyl monomer, polymerizing an amphoteric monomer or introducing an acidic group, a basic group, or both of such groups or an amphoteric group, selected depending on the properties, into a synthetic or natural polymer.

Typical examples of the above amphoteric polymer are as follows.

(1) Copolymer of acidic vinyl monomer with a basic vinyl monomer

A typical example of the amphoteric polymer of this type is one which is prepared by copolymerizing a monomer mixture comprising from 45 to 55% by mol of an acidic vinyl monomer or its salt and from 55 to 45% by mol of a basic vinyl monomer or its salt in the presence of a conventional radical polymerization initiator with or without using a conventional accelerator at 150° C. The molar ratio used herein is calculated assuming that each vinyl monomer has an acidic group or a basic group per molecule. When a monomer has two or more acidic or basic groups per molecule, it is therefore needed to appropriately control the molar ratio so as to adjust the substantial charge to almost 0.

The acidic vinyl monomer is a compound having acidic group(s) such as a carboxyl, sulfonate or phosphate group together with polymerizable vinyl group(s) in its molecule. Examples thereof include unsaturated monobasic acids such as acrylic acid, methacrylic acid, crotonic acid, vinylbenzoic acid, 2-acrylamide-2-methylpropanesulfonic acid, styrenesulfonic acid, vinylsulfonic acid, allylsulfonic acid, methacrylsulfonic acid and 3-methacrylpropanesulfonic acid, unsaturated dibasic acids such as itaconic acid, maleic acid and fumaric acid and monoesters of these acids. Further, salts of these acids such as the sodium, potassium and ammonium salts may be used.

The basic vinyl monomer is a compound having basic group(s) such as a primary amino group, a secondary amino group or a tertiary amino group together with polymerizable vinyl group(s) in a molecule. Examples thereof include dimethylaminoethyl methacrylate, diethylaminoethyl methacrylate, dimethylaminoethyl acrylate, diethylaminoethyl acrylate, dimethylaminopropyl acrylate, dimethylaminopropyl methacrylamide, dimethylaminopropyl acrylamide, 2-vinylpyridine, 4-vinylpyridine, dimethylallylamine, diallylmethylamine and quaternized products thereof.

The term quaternized products means hydrogenated, methylated and ethylated products where the counter anion is a halogen ion such as chlorine or bromine ion, a hydroxyl ion or a methyl sulfate group.

In addition to the above-mentioned acidic vinyl monomer and the basic vinyl monomer, another vinyl monomer copolymerizable with the acidic vinyl monomer and the basic vinyl monomer may be optionally copolymerized in the polymerization step as a third component. It is required, however, that the content of the third vinyl monomer not exceeds 60% by mol based on the total monomers.

The third vinyl monomer is selected from among monovinyl compounds polymerizable with the use of a radical polymerization initiator. Examples thereof include acrylates such as methyl acrylate and ethyl acrylate, methacrylates such as methyl methacrylate and ethyl methacrylate, styrene compounds such as styrene and α-methylstyrene, acrylamide, methacrylamide, vinyl ether and vinyl acetate.

(2) Polymer of amphoteric monomer

A typical amphoteric polymer of this type is one obtained by polymerizing an amphoteric monomer represented by the following general formula (XI) in the presence of a conventional radical polymerization initiator within a temperature range of from 20° to 130° C.

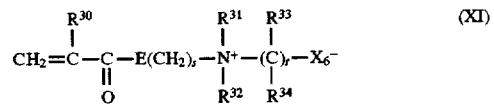

wherein $R^{30}$, $R^{33}$ and $R^{34}$ each represent a hydrogen atom or a methyl group;

$R^{31}$ and $R^{32}$ each represent a methyl or ethyl group;

E is —O— or —NH—;

$X_6$ is —$CO_2$, —$SO_3$ or —$PHO_3$; and s and t are each an integer of from 1 to 3.

The amphoteric monomer represented by the above general formula (XI) can be synthesized through a reaction between an appropriate aminoalkyl acrylate or methacrylate, or an aminoalkylamide and lactone, sultone or cyclic phosphide.

Examples thereof include 3-dimethyl (methacroyloxyethyl)ammonium propanesulfonate and 3-dimethyl(methacroylamidopropyl)ammonium propanesulfonate.

In addition to the above-mentioned amphoteric monomer, another vinyl monomer copolymerizable therewith may be optionally copolymerized in the polymerization step. It is required, however, that the content of such another vinyl monomer not exceeds 60% by mol based on the total monomers. This additional vinyl monomer is selected from among monovinyl compounds polymerizable with the use of a conventional radical polymerization initiator. Examples thereof include acrylates such as methyl acrylate and ethyl acrylate, methacrylates such as methyl methacrylate and ethyl methacrylate, styrene compounds such as styrene and α-methylstyrene, acrylamide, methacrylamide, vinyl ether and vinyl acetate.

The above cationic polymer or amphoteric polymer may be used either alone or as a combination of two or more thereof. The content thereof in the second pack preferably ranges from 0.01 to 10%, still more preferably from 0.1 to 5%, based on the total weight of the second pack. When the content of the polymer is smaller than the lower limit as defined above, no recognizable and long-lasting conditioning effect can be imparted. When the content thereof exceeds the upper limit, on the other hand, effects are not further improved.

When a direct dye is further added to the first pack of the keratinous fiber treating composition according to the present invention, colors of various tones can be imparted to keratinous fibers. Similar to the above cationic and amphoteric polymers, this direct dye can deeply penetrate into the keratinous fibers.

As direct dyes usable in the present invention, anthraquinone-, azo- and nitro-direct dyes having a bulky structure can be exemplified. Examples thereof include nitro-dyes such as 3-amino-4-hydroxynitrobenzene, 2-amino-5-hydroxynitrobenzene, 2-amino-3-hydroxynitrobenzene, 2-amino5-N,N-bis-β-hydroxyethylaminonitrobenzene, 2-amino-4-chloro-5-N-β-hydroxyethylaminonitrobenzene, 2-amino-4-methyl-5-N-β-hydroxyethylaminonitrobenzene, 3,4-bis-(N-β-hydroxyethylamino)nitrobenzene, 2-amino-4-methyl-5-N-β,γ-dihydroxypropylaminonitrobenzene, 2-amino-4-methyl-5-β-aminoethylaminonitrobenzene, 2-amino-4-hydroxynitrobenzene and, as still more preferable examples, 3,4diaminonitrobenzene, 2,5-diaminonitrobenzene, 2-amino-5-N-β-hydroxyethylaminonitrobenzene, 2-N-β-hydroxyethylamino-5-N,N-bis-β-hydroxyethylaminonitrobenzene, 2-N-methylamino-5-N,N-bis(β-hydroxyethyl)aminonitrobenzene, 2-N-methylamino-5-N-methyl-N-methyl-N-β-hydroxyethylaminonitrobenzene, 2-N-β-hydroxyethylamino-5-hydroxynitrobenzene, 3-methoxy-4-N-β-hydroxyethylaminonitrobenzene, 4-nitro-3-methylaminophenoxyethanol, 2-N-β-hydroxyethylamino-5-aminonitrobenzene, 2-N-β-hydroxyethylaminonitrobenzene, 3amino-4-N-β-hydroxyethyl-aminonitrobenzene, 3-β-hydroxyethyloxy-4-N-β-hydroxyethyl-aminonitrobenzene, 2amino-5-N-methylaminonitrobenzene, 2-amino-3-methylnitrobenzene, 2-N-β-hydroxyethylamino-5-β,γ-dihydroxypropyloxynitrobenzene, 3-hydroxy-4-N-β-hydroxyethylaminonitrobenzene, 3-hydroxy-4-aminonitrobenzene, 2,5-N,N'-β-hydroxyethylaminonitrobenzene, 2-N-methylamino-4-o-β,γ-dihydroxypropyloxynitrobenzene, 2-N-β-aminoethylamino-5-N,N'-bis(β-hydroxyethyl)aminonitrobenzene, 2-N-β-aminoethylamino-4-methoxynitrobenzene, and 2-N-β-aminoethylamino-5-β-hydroxyethyloxynitrobenzene; anthraquinone-direct dyes such as 1-amino-4-methylaminoanthraquinone and 1,4-diaminoanthraquinone; acid dyes such as Acid Red 27, Acid Red 51, Acid Red 18, Acid Red 92, Acid Red 94, Acid Red 52, Acid Yellow 23, Food Yellow 3, Food Green 3, Food Blue 2, Acid Blue 74, Acid Red 33, Acid Red 87, Acid Red 92, Acid Red 94, Acid Orange 7, Acid Red 95, Acid Yellow 73, Acid Yellow 3, Acid Green 25, Solvent Green 7, Acid Green 5, Acid Blue 5, Acid Blue 9, Acid Orange 24, Acid Violet 9, Food Red 6, Acid Red 26, Food Red 1, Acid Red 88, Acid Orange 20, Acid Yellow 40, Acid Yellow 1, Acid Yellow 36, Acid Yellow 11, Acid Green 1, Acid Green 3, Acid Violet 43, Acid Black 1, oil-soluble dyes such as Solvent Red 49, Solvent Red 48, Solvent Red 23, Solvent Red 72, Solvent Red 73, Acid Yellow 73, Solvent Yellow 33, Solvent Green 3, Solvent Violet 13, Solvent Red 24, Solvent Orange 7, Solvent Orange 2, Solvent Yellow 5, Solvent Yellow 6, Solvent Blue 63; basic dyes such as Basic Violet 10; basic dyes manufactured by Williams Co. such as Sienna Brown, Mahogany, Madder Red, Steel Blue and Straw Yellow; and disperse dyes such as Disperse Black 9, Disperse Blue 1, Disperse Blue 3, Disperse Violet 1 and Disperse Violet 4.

The content of these direct dyes may vary depending on the desired elasticity and color tone of the keratinous fibers. It is preferable that the first pack of the composition of the present invention contains from 0.08 to 5%, still more preferably from 0.15 to 3%, of the direct dye(s), based on the total weight of the first pack.

Further, the second pack of the keratinous fiber treating composition according to the present invention may contain various anionic surfactants, amphoteric surfactants and betaine-type surfactants in order to form a complex together with the cationic polymer or the amphoteric polymer contained in the second pack so as to modify the feel on the hair. Either one of these surfactants or a combination thereof may be used.

Specific examples of these surfactants include straight-chain or branched-chain alkylbenzenesulfonates, alkyl or alkenyl sulfates, ethylene oxide and/or propylene oxide-added alkyl or alkenyl sulfates, olefin sulfonates, alkane sulfonates, saturated or unsaturated fatty acids, ethylene oxide and/or propylene oxide-added alkyl or alkenyl ether carboxylates, α-sulfo fatty acid salt esters, amino acid surfactants such as amidoamino acids and acylated amino acids, phosphate surfactants, sulfosuccinic acid surfactants, taurine surfactants, amide ether sulfate surfactants, sulfonic acid surfactants, carbobetaine surfactants, sulfobetaine surfactants and amidobetaine surfactants. Either one of the above-mentioned anionic, amphoteric and betaine surfactants or a combination thereof may be used. The second pack preferably contains from 0.01 to 10%, still preferably from 0.1 to 5%, of one or more of these surfactants, based on the total weight of the second pack. When the content of the surfactant(s) is smaller than the lower limit defined above, no recognizable and long-lasting conditioning effect can be imparted. When the content exceeds the upper limit, on the other hand, the effects are not further improved. The ratio of cationic and/or amphoteric polymers to the anionic, amphoteric and/or betaine surfactant(s) may vary depending on the molecular weight. The ratio preferably ranges from 1/20 to 5/1, still more preferably from 1/10 to 3/1 (by weight).

The first pack and the second pack of the keratinous fiber treating composition of the present invention may be produced by a conventional method. In the present invention, the first pack and the second pack may further optionally contain additives commonly employed in the field of cosmetics, for example, thickeners such as hydroxyethyl cellulose, texture improvers such as silicones, perfumes, preservatives, UV absorbers, antioxidants and bactericides so long as the effects of the present invention are not deteriorated.

By using the keratinous fiber treating composition according to the present invention, keratinous fibers may be treated in the following manner. Namely, the keratinous fibers are treated with the first pack, allowed to stand for a definite time (10 to 60 minutes), optionally rinsed, typically with water, and treated with the second pack. To further improve the effects of the present invention, it is recommended that keratinous fibers are treated with the first pack, heated to 30° to 50° C. for 10 to 35 minutes, then treated with the second pack, allowed to stand at room temperature for 5 to 20 minutes and then rinsed with running water, followed by drying.

When keratinous fibers are treated with the keratinous fiber treating composition according to the present invention, the cationic polymer and the amphoteric polymer contained in the second pack penetrate into the keratinous fibers, which have been swollen with the first pack, to exert conditioning effects (softness, moistness, smoothness and ease of arrangement of the hair) on the keratinous fibers for a prolonged period of time. When a direct dye is further added to the first pack, various color tones can be imparted to the keratinous fibers, in addition to the above-mentioned conditioning effects.

To further illustrate the present invention in greater detail, and not by way of limitation, the following Examples will be given.

EXAMPLE 1

First packs (A-1, B-1, C-1 and D-1) and second packs (A-2, B-2, C-2 and D-2) as listed in Table 1 were prepared. The texture and softness of hair swatches treated with each of the above-mentioned compositions were evaluated. Table 3 summarizes the results.

TABLE 1

|  | Content (%) | | | |
| --- | --- | --- | --- | --- |
|  | A-1 | B-1 | C-1 | D-1 |
| 2-benzyloxy ethanol | — | — | — | 10.0 |
| ethanol | 20.0 | 20.0 | 20.0 | 15.0 |
| benzyl alcohol | 8.0 | 8.0 | 8.0 | — |
| lactic acid | 8.0 | — | 8.0 | 8.0 |
| sodium lactate | 1.0 | — | 1.0 | 1.0 |
| citric acid | — | 4.0 | — | — |
| sodium citrate | — | 0.1 | — | — |
| hydroxyethyl cellulose[1] | 1.0 | 1.0 | 1.0 | 1.0 |
| Acid Black 1 | — | — | 0.2 | 0.2 |
| water | the balance | do. | do. | do. |
| pH | 3.6 | 2.9 | 3.6 | 3.6 |

[1] Molecular weight: about 100,000 (weight average).

TABLE 2

|  | Content (%) | | | |
| --- | --- | --- | --- | --- |
|  | A-2 | B-2 | C-2 | D-2 |
| Merquat 100[1] | 0.3[6] | — | — | 0.3[6] |
| Polymer JR-400[2] | — | 0.4 | — | — |
| Plasize L-401[3] | — | — | 0.4[6] | — |
| Softazoline CL[4] | — | — | — | 3.0[6] |
| Softazoline LPB[5] | 0.3 | 0.3[6] | 0.3[6] | — |
| propylene glycol | 10.0 | 10.0 | 10.0 | 5.0 |
| cetostearyl alcohol | — | — | — | 4.0 |
| hydroxyethyl cellulose | 1.0 | 1.0 | 1.0 | — |
| water | the balance | do. | do. | do. |

[1] Dimethyldiallylammonium polymer (mfd. by Merck Inc.).
[2] Quaternium 19 (cationized cellulose mfd. by Union Carbide Co.).
[3] N-methacryloylethyl-N,N-dimethylammonium-α-N-methylcarboxy-betaine polymer (mfd. by Goou Chemicals Co., Inc.).
[4] 2-Cocoyl-N-carboxymethyl-N-hydroxyethylimidazolinium betaine (mfd. by Kawaken Fine Chemicals Co., Inc.).
[5] N-lauroylamidopropyl betaine (mfd. by Kawaken Fine Chemicals Co., Inc.).
[6] as a concentration of the active compound.

EVALUATION METHOD (1) Texture and softness of hair just after treating 4 g of the first pack was applied to 20 g of a shampooed hair swatch (length: 15 cm) and allowed to stand at 40° C. for 20 minutes. Next, 4 g of the second pack was applied thereto followed by allowing to stand at room temperature for 5 minutes. After washing with running water, the hair swatch was dried. The sample thus obtained was referred to as the hair just after treating.

For comparison, 4 g of the first pack A-1 was applied onto a similar hair swatch and allowed to stand at 40° C. for 20 minutes. Then the hair swatch was rinsed with running water and dried. Separately, 4 g of the second pack A-2 was applied onto another hair swatch and allowed to stand at room temperature for 5 minutes. Then the hair swatch was rinsed with running water and dried.

The texture and softness of each hair swatch were evaluated by 5 skilled panelists based on the following criteria.

Texture of hair

⊙: Very smooth and easily combed with the fingers.

○: Smooth and easily combed with the fingers.

Δ: Not smooth but somewhat rough.

x: Tangling and seriously rough.

Softness of hair

⊙: Much softer than untreated hair.

○: Softer than untreated hair.

Δ: Somewhat softer than untreated hair.

x: Comparable to untreated hair.

(2) Texture and softness of hair after shampooing 4 times

Each hair swatch employed in the above evaluation (1) was repeatedly washed with a commercially marketed shampoo and dried 4 times. Then the texture and softness were evaluated based on the following criteria with the use of an unshampooed hair swatch as a control.

As Table 3 shows, the invention cases are superior to the comparative ones in the texture and softness of the hair.

Texture of hair

○: Never differing from the control.

Δ: Somewhat inferior as compared with the control in flexibility and combing properties.

x: Remarkably inferior as compared with the control in flexibility and combing properties.

Softness of hair

○: Sufficiently soft similar to control.

Δ: Somewhat harder than control.

x: Remarkably harder than control.

TABLE 3

|  | Invention product | | | | | | | Comparative | |
| --- | --- | --- | --- | --- | --- | --- | --- | --- | --- |
|  | 1 | 2 | 3 | 4 | 5 | 6 | 7 | 1 | 2 |
| Treatment | A-1→A-2 | B-1→B-2 | C-1→C-2 | D-1→D-2 | A-1→D-2 | B-1→D-2 | C-1→D-2 | A-1 | A-2 |
| Immediately after treating: | | | | | | | | | |
| Texture | ⊙ | ○ | ⊙ | ⊙ | ⊙ | ⊙ | ⊙ | x | ○ |

TABLE 3-continued

| | Invention product | | | | | | | Comparative | |
| --- | --- | --- | --- | --- | --- | --- | --- | --- | --- |
| Treatment | 1 A-1→A-2 | 2 B-1→B-2 | 3 C-1→C-2 | 4 D-1→D-2 | 5 A-1→D-2 | 6 B-1→D-2 | 7 C-1→D-2 | 1 A-1 | 2 A-2 |
| Softness After shampooing 4 times: | ○ | ○ | ○ | ⊚ | ⊚ | ⊚ | ○ | x | Δ |
| Texture | ○ | ○ | ○ | ○ | ○ | ○ | ○ | x | x |
| Softness | ○ | ○ | ○ | ○ | ○ | ○ | ○ | x | x |

What is claimed is:

1. A two-pack keratinous fiber treating composition consisting of a first pack containing one or more organic solvents selected from the group consisting of benzyl alcohol, N-methylpyrrolidone, N-octylpyrrolidone and N-laurylpyrrolidone and one or more weak acids selected from the group consisting of citric acid, glycolic acid, succinic acid, tartaric acid, lactic acid, acetic acid, fumaric acid, malic acid, butyric acid, valeric acid, oxalic acid, maleic acid, phthalic acid, mandelic acid and phosphoric acid and a second pack containing a cationic polymer which is a diallyl quaternary ammonium salt polymer and an anionic surfactant, an amphoteric surfactant, or an anionic surfactant and an amphoteric surfactant;

wherein the total amount of the anionic surfactant, amphoteric surfactant, or combination thereof, is 0.01 to 10% by weight based on the total weight of the second pack;

wherein the amount of the organic solvents is 5 to 50% by weight based on the total weight of the first pack;

the amount of the one or more weak acids is 0.01 to 25% by weight based on the total weight of the first pack;

the first pack has a pH of 2.0 to 5.0;

and the total amount of the cationic polymer is 0.01 to 10% by weight based on the total weight of the second pack.

2. A method for treating keratinous fibers which comprises successively treating the keratinous fibers with a keratinous fiber treating composition which consists of a first pack containing one or more organic solvents selected from the group consisting of benzyl alcohol, N-methylpyrrolidone, N-octylpyrrolidone and N-laurylpyrrolidone and one or more weak acids selected from the group consisting of citric acid, glycolic acid, succinic acid, tartaric acid, lactic acid, acetic acid, fumaric acid, malic acid, butyric acid, valeric acid, oxalic acid, maleic acid, phthalic acid, mandelic acid and phosphoric acid and a second pack containing a cationic polymer which is a diallyl quaternary ammonium salt polymer and an anionic surfactant, an amphoteric surfactant, or an anionic surfactant and an amphoteric surfactant;

wherein the total amount of the anionic surfactant, amphoteric surfactant, or combination thereof, is 0.01 to 10% by weight based on the total weight of the second pack;

wherein the amount of the organic solvents is 5 to 50% by weight based on the total weight of the first pack;

the amount of the one or more weak acids is 0.01 to 25% by weight based on the total weight of the first pack;

the first pack has a pH of 2.0 to 5.0;

and the amount of the cationic polymer is 0.01 to 10% by weight based on the total weight of the second pack.

3. A two-pack keratinous fiber treating composition as claimed in claim 1, wherein the first pack further contains direct dyes in an amount of from 0.08 to 5% by weight based on the total weight of the first pack.

4. A method for treating keratinous fibers as claimed in claim 2, wherein the first pack further contains direct dyes in an amount of from 0.08 to 5% by weight based on the total weight of the first pack.

* * * * *